US012651335B2

(12) United States Patent
Garrett et al.

(10) Patent No.: US 12,651,335 B2
(45) Date of Patent: Jun. 9, 2026

(54) AUTOMATED CT CONTRAST DETECTION

(71) Applicant: Wisconsin Alumni Research Foundation, Madison, WI (US)

(72) Inventors: John W. Garrett, Middleton, WI (US); Perry J. Pickhardt, Madison, WI (US); B. Dustin Pooler, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 383 days.

(21) Appl. No.: 18/303,426

(22) Filed: Apr. 19, 2023

(65) Prior Publication Data

US 2024/0354936 A1 Oct. 24, 2024

(51) Int. Cl.
| | |
|---|---|
| *G06T 7/00* | (2017.01) |
| *A61B 6/00* | (2024.01) |
| *G06T 7/10* | (2017.01) |
| *G06V 10/74* | (2022.01) |
| *G16H 30/20* | (2018.01) |

(52) U.S. Cl.
CPC ........... *G06T 7/0012* (2013.01); *A61B 6/481* (2013.01); *G06T 7/10* (2017.01); *G06V 10/761* (2022.01); *G16H 30/20* (2018.01); *G06T 2207/10081* (2013.01); *G06T 2207/30101* (2013.01)

(58) Field of Classification Search
CPC ........... A61B 6/032; A61B 6/481; A61B 6/50; A61B 6/504; A61B 6/5252; G06V 10/761; G16H 30/20; G06T 2207/10081; G06T 2207/30101; G06T 7/0012; G06T 7/10; G06T 7/11

USPC .......................................................... 382/131
See application file for complete search history.

(56) References Cited

U.S. PATENT DOCUMENTS

| | | | | |
|---|---|---|---|---|
| 9,384,555 | B2 * | 7/2016 | Razeto | A61B 6/507 |
| 2005/0033159 | A1 * | 2/2005 | Mistretta | G01R 33/563 |
| | | | | 600/420 |
| 2005/0080328 | A1 * | 4/2005 | Vass | A61B 90/36 |
| | | | | 600/407 |
| 2007/0189443 | A1 * | 8/2007 | Walter | G06T 7/136 |
| | | | | 378/4 |
| 2012/0172718 | A1 * | 7/2012 | Huang | G06T 7/11 |
| | | | | 600/425 |
| 2016/0000945 | A1 * | 1/2016 | Nedergaard | A61P 25/16 |
| | | | | 604/9 |
| 2016/0180525 | A1 * | 6/2016 | Reynolds | G06T 7/0016 |
| | | | | 382/131 |
| 2018/0078232 | A1 * | 3/2018 | Silbert | G06T 7/0016 |
| 2019/0290222 | A1 * | 9/2019 | Proksa | A61B 6/482 |

(Continued)

OTHER PUBLICATIONS

Criminisi, et al., "A Discriminative-Generative Model for Detecting INtravenous Contrast in CT Images," Medical Image Computing and Computer-Assisted Intervention—MICCAI 2011, Lecture Notes in Computer Science, vol. 6893, 2011 (pp. 49-57).

*Primary Examiner* — Matthew C Bella

(74) *Attorney, Agent, or Firm* — Boyle Fredrickson, S.C.

(57) ABSTRACT

A system for automatically determining whether a CT image was taken with or without contrast media uses a segmentation to isolate voxels of a vascularized structure and simple statistical thresholding of the attenuation values of the isolated voxels to provide transparent and robust discrimination. In some embodiments, the phase of the contrast injection can be deduced from a degree of variation in attenuation of the isolated organ voxels.

19 Claims, 2 Drawing Sheets

(56)  References Cited

U.S. PATENT DOCUMENTS

2020/0294653  A1*  9/2020  Gotman ................. G16H 30/20
2023/0169633  A1*  6/2023  Freiman ............... G06T 7/0012
                                                    382/128

* cited by examiner

AUTOMATED CT CONTRAST DETECTION

CROSS REFERENCE TO RELATED APPLICATION

Background of the Invention

The present invention relates generally to computed tomography (CT) machines and in particular to a system for determining whether images acquired on a CT machine were taken with an injected contrast medium.

Computed tomography uses x-rays to acquire projections of attenuation data through a patient at multiple angles, for example, in successive slices, to reconstruct a volumetric x-ray image of the patient. Conventionally, this volumetric representation is expressed as a set of voxels each located in Cartesian space and having associated attenuation values, for example, Hounsfield units (HU), quantitative values that are calibrated to be consistent across different machines.

Typically, these values may be stored in digital form, according to the Digital Imaging and Communications in Medicine (DICOM) standard, for later retrieval and review. In the DICOM standard, image data is linked to image metadata in a DICOM header providing additional information about the image data including, for example, CT machine setting, such as x-ray energy and orientation, and imaging protocol information such as whether the patient received an injection during the imaging of contrast-enhancing materials intended to enhance x-ray attenuation of vascularized structures in the body, and by design intended to materially alter the attenuation value of specific tissues . . . .

Information about contrast media is normally entered manually (by the technologist acquiring the scan or from original orders placed in the electronic medical record that may change) and thus may be subject to error. At least one study suggests that contrast data is recorded inaccurately in as much as 20% of CT images. See, Criminisi A, Juluru K, Pathak S, "A discriminative-generative model for detecting intravenous contrast in CT images", Med Image Comput Comput Assist Interv., 2011; 14 (Pt 3):49-57, doi: 10.1007/978-3-642-23626-6_7. PMID: 22003683.

A CT contains a wealth of information that could be used for opportunistic diagnosis of medical conditions other than the condition motivating the image acquisition. This opportunistic analysis of a CT is practical because of the ability to train machine learning systems to perform multiple diagnostic analyses rapidly at low marginal cost.

Unfortunately, the high incidence of errors in the metadata associated with CT images, and in particular errors in recording contrast media usage, can adversely affect collection of accurate training data for diagnostic artificial intelligence systems or the selection of appropriate algorithms or correction schemes for making the particular diagnoses mentioned above. One approach to addressing this problem, described in the above-cited reference, applies a preliminary machine learning model to the images to deduce contrast information from the image itself. This additional layer of machine learning decreases the transparency of the diagnostic process and introduces a new source of error. The accuracy of this approach as currently reported is approximately 91%.

SUMMARY OF THE INVENTION

The present invention provides an improved system identifying whether an image was taken with contrast media by performing a statistical analysis on isolated voxels of a "bellwether" vascularized structure such as the spleen. The simple statistical analysis allows improved oversight of the identification process, reducing the introduction of additional errors. Preliminary analysis indicates that an accuracy of greater than 99% can be obtained.

More specifically, the present invention provides a system for CT contrast detection employing an electronic computer to receive a digitized CT image describing a volume of voxels having x-ray attenuation values. The received data is segmented to isolate voxels of at least one predetermined vascularized structure capable of receiving an injected contrast medium from surrounding tissue, and a statistical measure of the x-ray attenuation values of the isolated voxels is made. This extracted statistical measure is compared to a predetermined threshold adapted to distinguish digitized CT images taken with a contrast medium and digitized CT images taken without a contrast medium, and the result of the comparison is output.

It is thus a feature of at least one embodiment of the invention to use the segmentation process to allow contrast media used to be identified with a simple and transparent statistical calculation.

The computer may further execute to compare a second measure of the isolated voxels (other than the extracted statistical measure) to a corresponding predetermined expected range to provide an error output indicating that the measure of segmentation is not within the expected range.

It is thus a feature of at least one object of the invention to allow confirmation of correct operation of the segmentation process.

The second measure of the isolated voxels may indicate a volume of the at least one predetermined vascularized structure.

It is thus a feature of at least one embodiment of the invention to provide a method of confirming both that the segmentation process was not over inclusive and that the vascularized structure was correctly identified or of sufficient size for analysis.

The output is provided as metadata attached to the received digitized CT image, for example, in a DICOM header.

It is thus a feature of at least one embodiment of the invention to provide a method of automatically correcting large sets of DICOM images, for example, that may be formed into training sets for machine learning.

The statistical measure provides an averaging of attenuation values of the isolated voxels, for example, a median value.

It is thus a feature of at least one embodiment of the invention to provide a simple statistical measure of well-defined operation in contrast to the complex and largely unreviewable processes of machine learning.

The predetermined vascularized structure maybe limited to a single organ, for example, the spleen.

It is thus a feature of at least one embodiment of the invention to operate with a limited volume of CT data.

In some cases the electronic computer may further execute to extract an additional statistical measure of the x-ray attenuation values of the isolated voxels indicating a variation in attenuation values. This additional statistical measure may be compared to a corresponding additional threshold to determine whether the digitized CT images were taken during an arterial phase of a contrast medium injection and digitized CT images were taken during a venous phase of the contrast medium injection.

It is thus a feature of at least one embodiment of the invention to allow extraction of the arterial phase from a CT image.

In some embodiments, the electronic computer may receive a radiation energy value associated with the received digitized CT image and may obtain the predetermined threshold as a function of the received radiation energy value.

It is thus a feature of at least one embodiment of the invention to provide a system that can work with a variety of different x-ray spectra.

These particular objects and advantages may apply to only some embodiments falling within the claims and thus do not define the scope of the invention.

DETAILED DESCRIPTION OF THE PREFERRED EMBODIMENT

Figure 1:
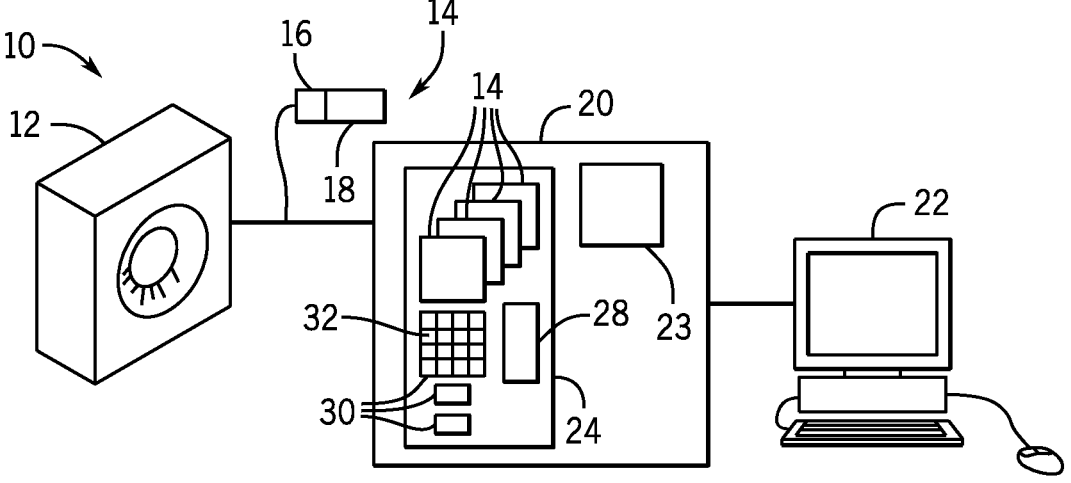
FIG. 1 is block diagram of the present invention showing a CT machine for acquiring volumetric images that may be relayed to an electronic computer system for storage and analysis.

Referring now to FIG. 1, a system 10 for detecting the use of contrast media in CT images may employ a CT machine 12 of the type generally understood in the art for acquiring volumetric x-ray attenuation data of a patient (not shown). As is generally understood in the art, this attenuation data is acquired through a mathematical reconstruction of x-ray projections taken at a range of angle about the patient which results in a "CT image" characterizing x-ray attenuation values for set of voxels over a range of associated Cartesian coordinate values within an imaging volume.

The voxel attenuation values may be expressed in Hounsfield units (HU) being proportional to the absorption or attenuation of the x-ray beam at the particular voxel and referenced to a value of zero for an attenuation equal to the attenuation of water so that water has an HU value of zero . . . .

The data of the CT image may be transferred from the CT machine 12 and later stored as a DICOM file 14 providing a header 16 linked to image data 18, the latter comprising the voxel attenuation values identified to voxels. The header 16 generally provides metadata associated with the image data 18 including information about the operating parameters of the CT machine 12 such as the x-ray tube energy in peak kilovoltage (KVp) derived automatically from the CT machine 12 as well as manually entered information about whether a contrast agent was administered to the patient during scanning.

The DICOM file 14 may be received by a computer system 20 representing one or more computer devices operating to provide a file server for storing the DICOM data and in the capacity of a user workstation for processing the DICOM files 14 and communicating with a user terminal 22. The computer system 20 may include one or more processors 23 communicating with an electronic memory 24 that may hold multiple DICOM files 14, for example, in a database structure, as well as various data values 30 and constants including an energy data table 32 such as will also be described below. The electronic memory 24 may further hold a program 28 executed by the processors 23 and implementing the present invention as will be described below.

Figure 2:
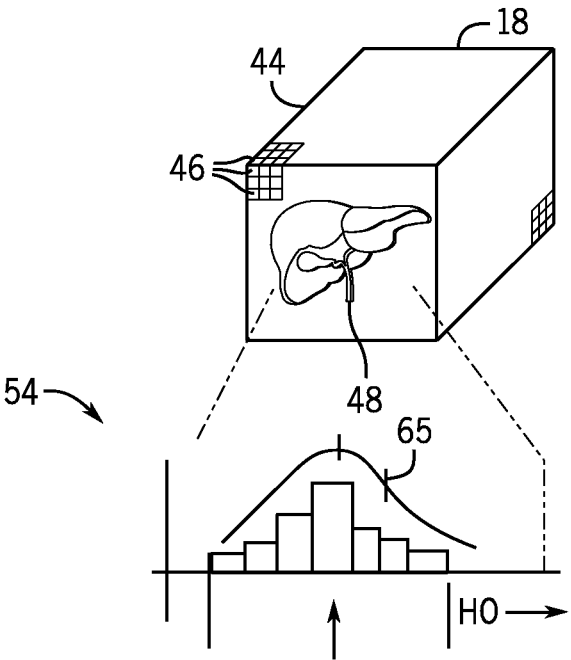
FIG. 2 is a diagrammatic representation of a volumetric data set acquired with the CT machine of FIG. 1 representing a CT image and showing, as an inset, a histogram of attenuation values analyzed with respect to the statistical median and the standard deviation.
Figure 3:
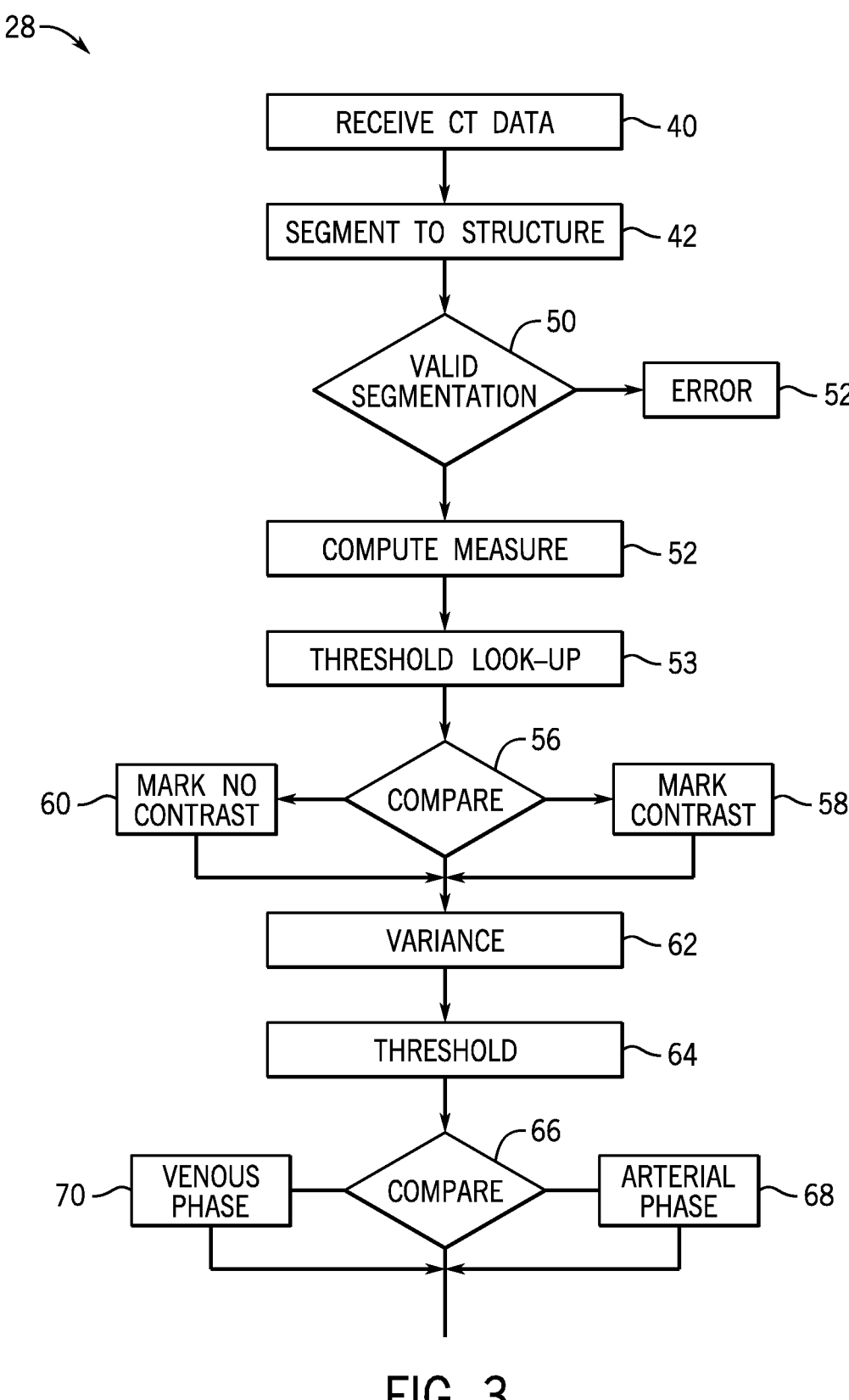
FIG. 3 is a flowchart of the process steps implemented by programming of the electronic computer system of FIG. 1 processing a CT image of FIG. 2.

Referring now also to FIGS. 2 and 3, as indicated by process block 40, the program 28 as executed may receive a CT image represented by a DICOM file 14, for example, associated with a patient for whom a clinical diagnosis is to be made.

The image data 18 of the DICOM file 14 may then be segmented per process block 42 to identify a predefined vascularized structure 48, for example, an organ such as the spleen or kidney or other highly vascularized structure such as the aorta, whose image will be sensitive to contrast media. The segmentation process of process block 40 may receive an input indicating this desired organ or structure for segmentation, or in some embodiments, may receive the identification of multiple desired organs or structures. Generally, the term vascularized structure is intended to indicate structure that has a substantial volume of blood flow that would receive an injected contrast medium to invoke a readily detectable change in HU values of the structure 48 of those voxels 46. Typically the average attenuation of the tissues of such structures would be expected to see a change of greater than 20 HU or more than 10% in average contrast with an injected contrast material.

Before the segmentation process, the CT images data 18 may be adjusted, for example, to a standard slice thickness such as 3 mm or to normalize the HU.

The segmentation process considers both the attenuation of the voxels 46 and their physical location and may use any of a number of existing segmentation programs for that purpose. In one embodiment, the segmentation may use the process described in Lec S, Elton D C, Yang A H, Koh C, Kleiner D E, Lubner M G, Pickhardt P J, Summers R M, "Fully Automated and Explainable Liver Segmental Volume Ratio and Spleen Segmentation at CT for Diagnosing Cirrhosis", Radiol Artif Intell., 2022 Aug. 24; 4 (5):e210268. doi: 10.1148/ryai.210268, PMID: 36204530; PMCID: PMC9530761. This reference is hereby incorporated by reference in its entirety.

The segmentation excludes tissue surrounding the vascularized structure to provide a more sensitive measurement and produces a segmented volume typically including less than 70% of voxels 46 of the image data 18 and more typically less than 50% of those voxels 46.

At decision block 50, an accuracy of the segmentation process and a confirmation that the desired vascularized structure 48 is available in the patient is assessed by extracting a corroborating measure and outputting that to the user terminal 22 and making an automatic evaluation of that corroborating measure against a predefined standard range of values. Most simply, the corroborating measure will be a volume of tissue in the segmented vascularized structure 48 compared to a range of values associated with that particular structure 48. For example, when the vascularized structure 48 is the spleen, decision block 50 may evaluate the volume of the segmented tissue to determine that it is at least 50 mL (confirming that there has not been a splenectomy) and more specifically is not outside of a predetermined range, for example, 50-5500 mL for a spleen.

If at decision block 50, the measured volume does not fit within the range associated with the identified vascularized structure 48, the program 28 proceeds to process block 52, for example, to report an error on the user terminal 22 of FIG. 1 and optionally to mark the error in the header 16 of the DICOM file 14 or to call the particular DICOM file 14 from a training set.

It is contemplated that at decision block 56, the program 28 may also look at other corroborating information obtained from the segmentation of process block 42, including, for example, a confidence interval which may be available in certain segmentation processes, or, for example, to confirm that the CT image has adequate anatomical coverage of the vascularized structure 48 with sufficient margins of exterior tissue. These measures may also be compared against predetermined ranges to indicate an error at process block 52 if those ranges are not satisfied. Optionally, an image revealing the segmentation can be output on the user terminal 22 for manual verification, and an input from the user may invoke process block 52.

If at decision block 50, the segmentation appears to be valid, then at decision block 52, a statistical analysis of the voxels 46 included within the segmentation of the structure 48 is performed. In one embodiment this analysis may take the form of determining a median value of the HU data of the voxels for the spleen. Such a median value considers a logical histogram 54 having a range of HQ units and a frequency of those voxels 46 within bins being subcategory ranges of HU values. The median value selects the midpoint between the range extremes of the histogram 54.

At succeeding process block 53, a median threshold value is selected according to the x-ray energy associated with the DICOM file 14 being processed as is typically stored in the DICOM header 16. In one nonlimiting example, a threshold value of 65 HU may be used for CT images of the spleen taken with x-ray energies having a spectrum equivalent to that obtained with a tube voltage of 120 KVP. This value may be from the energy data table 32 of FIG. 1 which may provide a set of threshold values for different values of x-ray tube energy and optionally also for different vascularized structures 48. The invention also contemplates that special threshold values may be obtained for dual energy acquisitions. These threshold values may be determined empirically by manually analyzing multiple DICOM datafiles 14.

At succeeding decision block 56, the statistical measure of process block 52 is compared to the threshold of process block 53. If the statistical measure is greater than the threshold, the DICOM header 16 may be corrected to indicate an IV contrast agent was used per process block 58. Conversely if the statistical measure is less than the threshold, the header 16 may be corrected to indicate that a contrast media was not used. This information may also be provided to the user terminal 22 for confirmation or viewing by the healthcare professional who may override these determinations.

Referring still to FIGS. 2 and 3, in either case of reaching process block 58 or process block 60, optionally, at a succeeding process block 62, a second statistical measurement may be made of the segmented data of the vascularized structure 48 to determine how uniform the attenuation values of the voxels 46 may be. In one embodiment, this uniformity may be expressed by determining a standard deviation 65 of the values of the histogram 54. At process block 64, a corresponding standard deviation threshold for comparison purposes may be established, for example, unique to the particular structure 48 using a corresponding extension on the energy data table 32 of FIG. 1.

At decision block 66, analogous to this decision block 56, the statistical measure of process blocks 62 is compared against the threshold of process block 64 to determine a likely phase of the contrast media in the acquired image. If the variance is greater than the threshold, indicating that the contrast media is not uniformly distributed in the vascularized structure 48, this suggests that the image was taken during the arterial phase as indicated by process block 68. Alternatively, if the variance is lower than the threshold of process block 64, there is a likelihood that the image was acquired during the venous phase 70 as indicated at process blocks 70. These phases indicate how far the contrast media has traveled within the body and may be provided to the user terminal 22 and/or incorporated into the header 16.

The program 28 may thus serve to confirm a correctness of the DICOM header 16 for building training sets that use this data of the header 16 in machine learning for opportunistic diagnosis. Such diagnosis builds machine learning models that can make ancillary measurements of bone density, body fat, muscle bulk, measurements of the liver for size attenuation or contour abnormalities that may indicate disease processes such as steatosis or cirrhosis, as well as a variety of other diagnoses that may be unrelated to the motivating diagnosis of the CT image.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112 (f) unless the words "means for" or "step for" are explicitly used in the particular claim.

What we claim is:

1. A system for CT contrast detection comprising:
an electronic computer executing a program stored in non-transitory memory to:
receive a digitized CT image in electronic format describing a volume of voxels having x-ray attenuation values, the digitized CT image being without categorization as to whether it was obtained with or without contrast medium;
perform a segmentation of the voxels in the electronic format to isolate voxels of at least one predetermined vascularized structure capable of receiving an injected contrast medium from surrounding tissue;
extract a statistical measure of the x-ray attenuation values of the isolated voxels in the electronic format;
compare the extracted statistical measure to a predetermined threshold adapted to distinguish digitized CT images taken with a contrast medium and digitized CT images taken without a contrast medium; and
provide an output indicating whether the digitized CT image was obtained with or without contrast medium.

2. The system of claim 1 wherein the electronic computer further executes the program to compare a second measure of the isolated voxels, other than the extracted statistical measure, to a predetermined expected range of measures to provide an error output indicating that the second measure of segmentation is not within the expected range.

3. The system of claim 2 wherein the error output is adapted to inform a healthcare professional that the system cannot reliably determine whether the received digitized CT image was taken with or without a contrast medium.

4. The system of claim 2 wherein the second measure of the isolated voxels indicates a volume of the at least one predetermined vascularized structure.

5. The system of claim 1 wherein the output is provided as metadata attached to the received digitized CT image.

6. The system of claim 5 wherein the metadata is a DICOM header of the received digitized image.

7. The system of claim 1 wherein the statistical measure provides an averaging of attenuation values of the isolated voxels.

8. The system of claim 7 wherein the averaging is a median value.

9. The system of claim 1 wherein the predetermined vascularized structure is limited to a single organ.

10. The system of claim 9 wherein the organ is a spleen.

11. The system of claim 1 wherein the electronic computer further executes the program to extract a second statistical measure of the x-ray attenuation values of the isolated voxels indicating a variation in attenuation values; and compare the extracted second statistical measure to a second predetermined threshold adapted to distinguish digitized CT images taken during an arterial phase of a contrast medium injection and digitized CT images taken during a venous phase of the contrast medium injection.

12. The system of claim 11 wherein the second statistical measure is standard deviation.

13. The system of claim 1 wherein the electronic computer further executes the program to receive a radiation energy value associated with the received digitized CT image and obtains the predetermined threshold as a function of the received radiation energy value.

14. A method of automatic CT contrast detection comprising:

executing a program stored in non-transitory memory with an electronic processor to:
receive at an input circuit a digitized CT image in electronic format describing a volume of voxels having x-ray attenuation values uncharacterized with respect to whether the digitized CT image was obtained with or without contrast medium;
perform a segmentation of the voxels to isolate voxels in the electronic format of at least one predetermined vascularized structure capable of receiving an injected contrast medium;
extract a statistical measure of the x-ray attenuation values of from the isolated voxels in the electronic format;
compare the extracted statistical measure to a predetermined threshold adapted to distinguish digitized CT images taken with a contrast medium and digitized CT images taken without a contrast medium; and
provide an output indicating whether the digitized CT image was obtained with or without contrast medium.

15. The method of claim 14 wherein the electronic computer further executes the program to compare a second measure of the isolated voxels other than the extracted statistical measure to a predetermined expected range of measures to provide an error output indicating that the measure of segmentation is not within the expected range.

16. The method of claim 15 wherein the second measure of the isolated voxels indicates a volume of the at least one predetermined vascularized structure.

17. The method of claim 15 wherein the organ is a spleen.

18. The method of claim 15 wherein the electronic computer further executes the program to extract a second statistical measure of the x-ray attenuation values of the isolated voxels indicating a variation in attenuation values; and compare the extracted second statistical measure to a second predetermined threshold adapted to distinguish digitized CT images taken during an arterial phase of a contrast medium injection and digitized CT images taken during a venous phase of the contrast medium injection.

19. The method of claim 14 wherein the electronic computer further executes the program to receive a radiation energy value associated with the received digitized CT image and obtains the predetermined threshold as a function of the received radiation energy value.

* * * * *